United States Patent [19]
Elias

[11] Patent Number: 5,908,151
[45] Date of Patent: Jun. 1, 1999

[54] CAPACITOR FOR AN IMPLANTABLE CARDIAC DEFIBRILLATOR

[75] Inventor: William H. Elias, Six Mile, S.C.

[73] Assignee: Pacesetter, Inc., Sunnyvale, Calif.

[21] Appl. No.: 08/939,181

[22] Filed: Sep. 29, 1997

Related U.S. Application Data

[62] Division of application No. 08/657,086, Jun. 3, 1996, Pat. No. 5,801,917.

[51] Int. Cl.⁶ ...................................................... B23K 20/10
[52] U.S. Cl. ................................... 228/110.1; 228/179.1; 228/190
[58] Field of Search ............................. 228/110.1, 179.1, 228/190; 361/532, 533, 535; 29/25.03, 25.42

[56] References Cited

U.S. PATENT DOCUMENTS

| | | | |
|---|---|---|---|
| 4,633,368 | 12/1986 | Frederick | 361/328 |
| 4,814,939 | 3/1989 | Box, Jr. | 361/307 |
| 5,131,388 | 7/1992 | Pless et al. | 128/419 D |
| 5,522,851 | 6/1996 | Fayram | 607/5 |
| 5,808,857 | 9/1998 | Stevens | 361/503 |

*Primary Examiner*—Samuel M. Heinrich
*Attorney, Agent, or Firm*—Steven M. Mitchell

[57] ABSTRACT

A capacitor and a method for making the capacitor using ultrasonic welding to join the cathode layers together are provided. The capacitor includes a housing defining a chamber with a step provided at an inner portion of the housing. A plurality of capacitor layers each including a cathode foil, a separator and an anode foil, each having alignment holes therein to precisely fit with alignment elements housing, is positioned within the chamber, with the alignment holes mating with the alignment elements. The housing is electrically conductive for connection to the cathode foils. Each cathode foil includes a cathode tab which extends away from the foil. The cathode tabs are pressed together and ultrasonically welded to the housing step abutting the periphery of the interior of the housing.

2 Claims, 4 Drawing Sheets

CAPACITOR FOR AN IMPLANTABLE CARDIAC DEFIBRILLATOR

RELATED APPLICATIONS

This is a divisional of application Ser. No. 08/657,086, filed on Jun. 3, 1996, now U.S. Pat. No. 5,801,917.

This application is related to U.S. patent application Ser. No. 08/350,853, filed Dec. 6, 1994 now U.S. Pat. No. 5,522,857, and to U.S. patent application Ser. No. 08/567,460, filed Dec. 5, 1995 now abandoned.

FIELD OF THE INVENTION

The invention relates to capacitors, and more particularly to capacitors for implantable cardiac defibrillators.

BACKGROUND AND SUMMARY OF THE INVENTION

Defibrillators are implanted in patients susceptible to cardiac arrhythmias or fibrillation. Such devices provide cardioversion or defibrillation by delivering a high voltage shock to the patient's heart, typically about 500–750 V. High voltage capacitors are used in defibrillators to accumulate the high voltage charge following detection of a tachyarrhythmia. It is desirable to make implantable devices as small as possible, with slim, flat packages being desired for pectorally implanted defibrillators. Therefore, flat capacitors have been developed to avoid the disadvantages of traditional cylindrical aluminum electrolytic capacitors.

Such a flat capacitor is disclosed in U.S. Pat. No. 5,131,388 to Pless et al., which is incorporated herein by reference. Flat capacitors include a plurality of layers laminarly arranged in a stack. Each layer includes an anode and a cathode, with the anodes and cathodes being commonly connected to respective connectors. The layers may be cut in nearly any shape, to fit within a similarly shaped housing designed for a particular application. The capacitance of such a device is proportional to the number of layers, and to the area of each layer, providing significant design flexibility. However, current flat capacitors are not as manufacturable as would be desirable. Misalignment of layers can cause shorting between the edges of anodes and cathodes, and with the walls of a metallic housing. Precision assembly by hand is required, increasing manufacturing costs. The housing size must also be increased to provide tolerance for alignment errors, resulting in a bulkier device. The thin cathode layers must be efficiently joined together and coupled to one electrode of the capacitor.

The present invention overcomes the limitations of the prior art by providing a capacitor and a method for making the capacitor using ultrasonic welding to join the cathode layers together. The capacitor includes a housing defining a chamber with a step provided at an inner portion of the housing. A plurality of capacitor layers each including a cathode foil, a separator and an anode foil, each having alignment holes die cut therein to precisely fit with alignment elements housing, is positioned within the chamber, with the alignment holes mating with the alignment elements. The housing is electrically conductive for connection to the cathode foils. Each cathode foil includes a cathode tab which extends away from the foil. The cathode tabs are pressed together and ultrasonically welded to the housing step abutting the periphery of the interior of the housing.

DETAILED DESCRIPTION OF A PREFERRED EMBODIMENT

Figure 1:
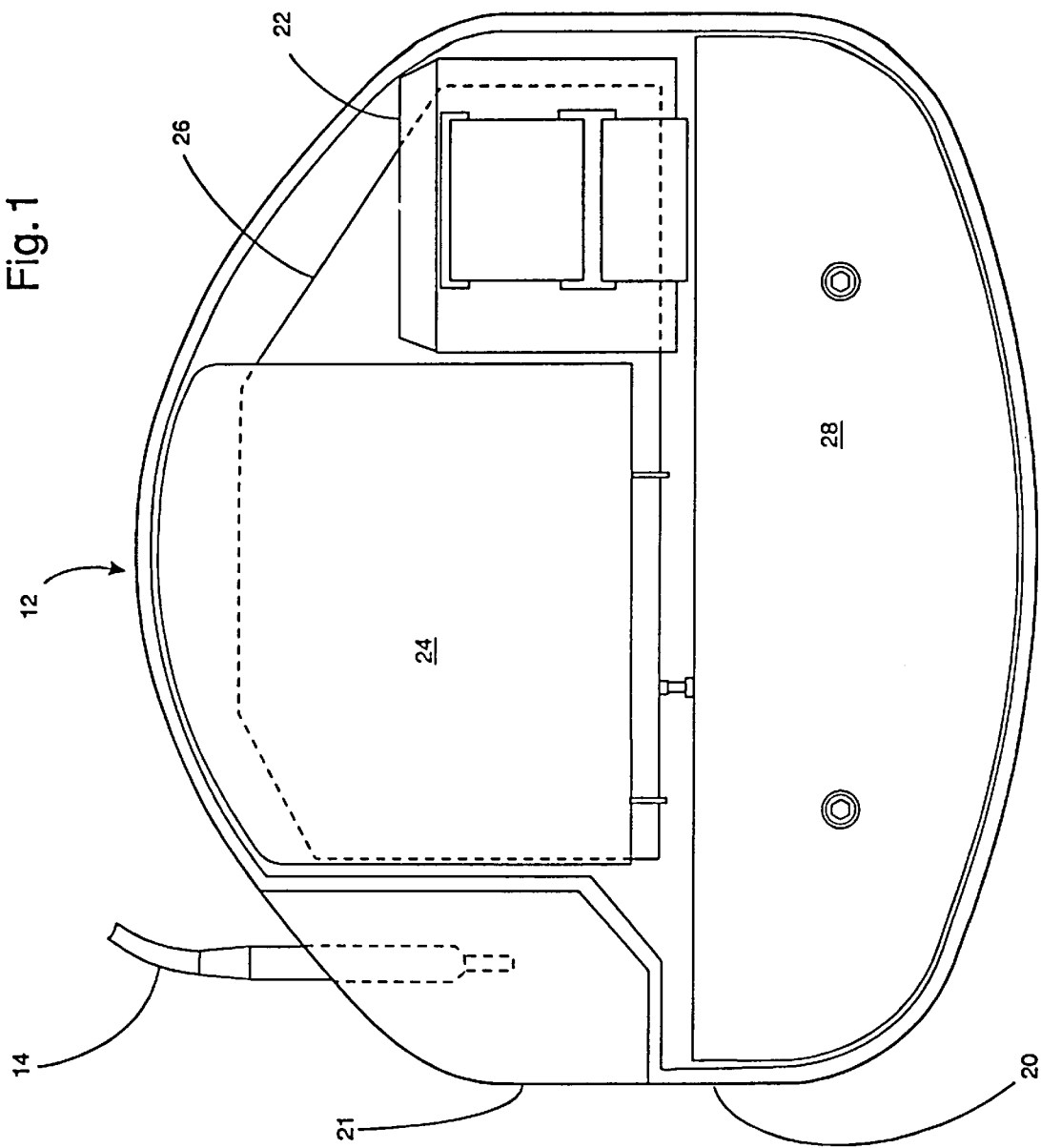
FIG. 1 shows an implantable defibrillator having capacitors according to the present invention.

FIG. 1 illustrates a defibrillator 12 for pectoral implantation. A single pass endocardial lead set 14 extends from the unit, through the patient's subclavian vein, and into the patient's heart. The defibrillator 12 includes an outer housing 20 that includes a header 21 for attachment of the lead set 14. The housing 20 contains a transformer 22, a battery 24, control circuitry 26, and two capacitors 28 (only one shown.) The battery provides electrical energy to charge the capacitor when needed so that it may provide a high voltage shock. The control circuitry 26 connects to the lead set 14 so that it may sense and analyze electrical signals from the heart, and control the delivery of a an appropriate therapy such as a high voltage shock.

Figure 2:
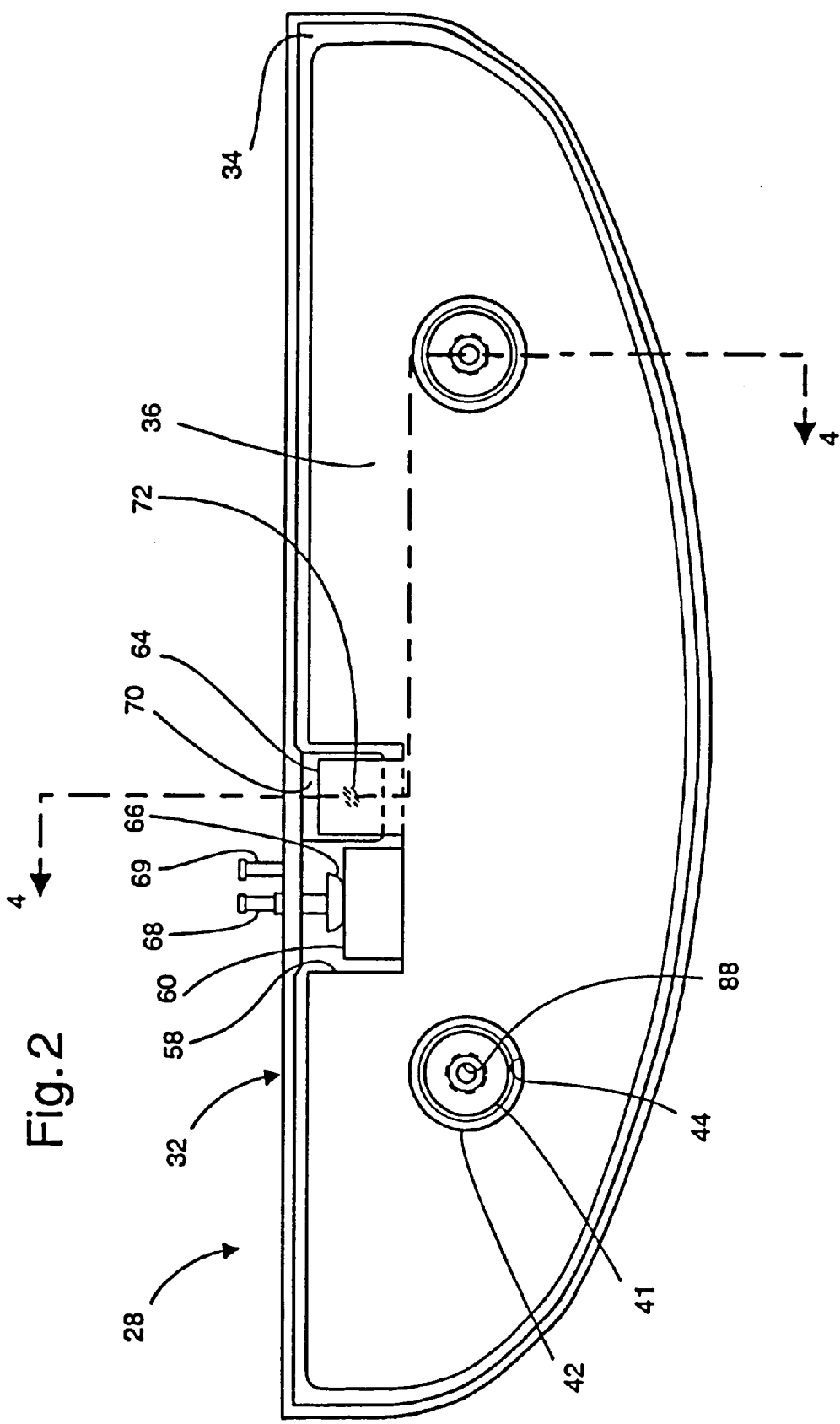
FIG. 2 is a plan view of the interior of the capacitor of FIG. 1.

FIG. 2 illustrates in detail the construction of the capacitor 28, which may be designed as virtually any flat shape to conform to a desired housing shape. The capacitor includes a metallic housing 32 defining a chamber 34, in which resides a capacitor stack 36. The housing includes a pair of alignment bosses 40, 41 which are encompassed by plastic insulating sleeves 42. The stack defines a pair of alignment holes 44 that closely receive the sleeves, providing accurate registration between the stack and the housing.

Figure 3:
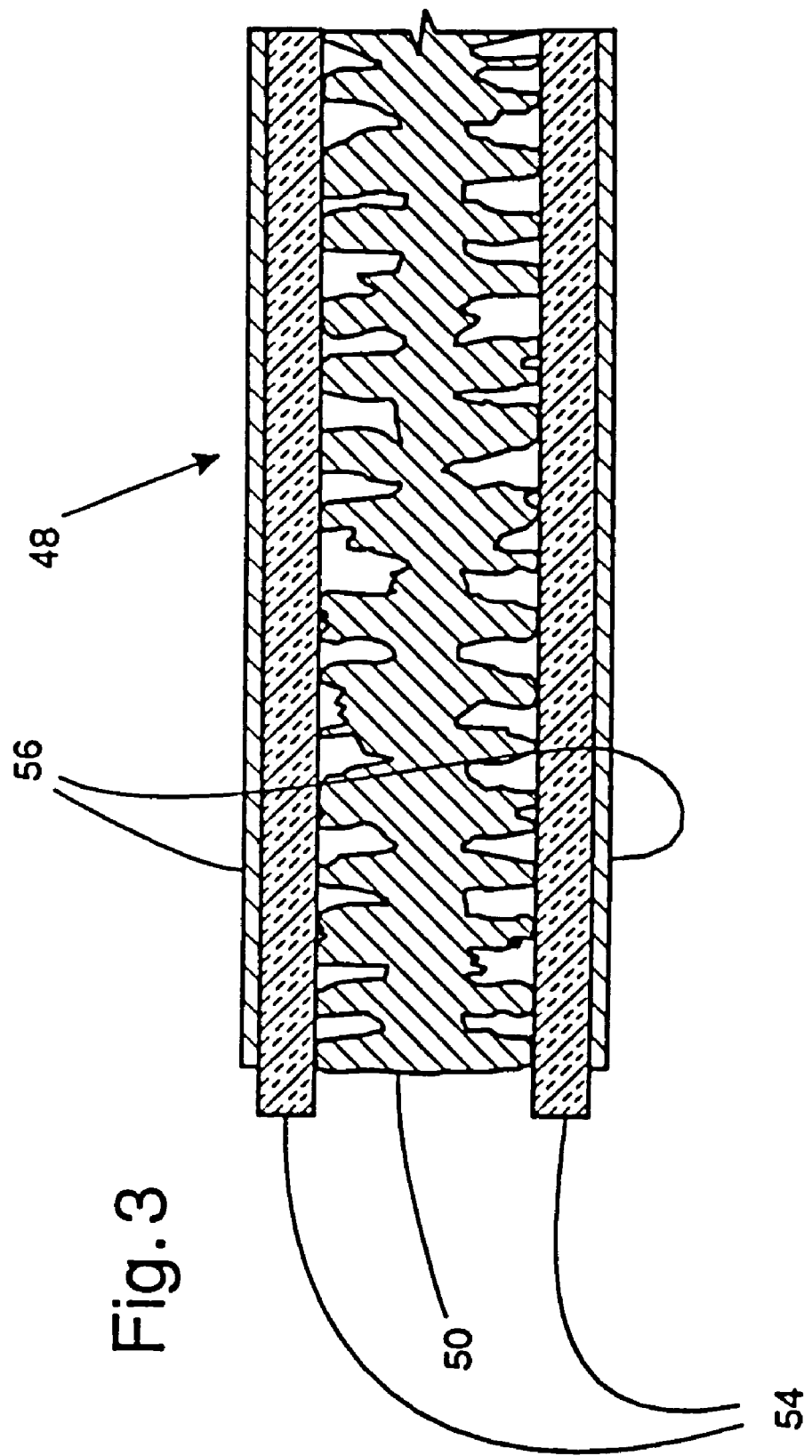
FIG. 3 is a cross sectional side view of a single capacitor layer.

The capacitor stack 36 is formed of a number of essentially identical flat capacitor layers 48 whose electrical elements are connected in parallel. The number of layers determines the capacitance and thickness of the device; in the preferred embodiment, 13 layers are used. As shown in FIG. 3, each layer 48 is a sandwich of sheets: a central anode 50 that is highly etched on both major surfaces, a pair of insulating paper sheets or separators 54 covering the opposite sides of the anode, and a pair of aluminum cathode sheets 56 covering the paper sheets. In the preferred embodiment, each layer 48 comprises a double anode capacitor wherein the anode 50 is made of two 0.0043 inch thick sheets back-to-back of deeply etched ultra pure aluminum with a grain structure that is perpendicular to the surface of each sheet. Each paper sheet is 0.002 inch thick, and each cathode sheet is 0.0006 inch thick. At the periphery, the paper sheets extend slightly beyond the cathode and anode to prevent electrical shorting due to any misalignment. The etched anode layer can be "formed" by passing a current through the anode and a cathode in the presence of an electrolyte. This generates an oxide layer that functions as a dielectric. The forming can be done before or after assembly of the stack. Once the capacitor is assembled and sealed, an electrolyte is injected into the chamber through a hole in the housing which is then sealed.

As shown in FIG. 2, each of the layers 48 has a cutout region 58 at its periphery, with the cutouts of each layer being aligned when the sheets are installed in the housing to provide space for electrical connections. The anodes 50 include anode tabs 60 extending into the cutout in registration with each other. Similarly, the cathodes 56 include cathode tabs 64 that extend into the cutout region in registration with each other, but spaced apart from the anode tabs to allow separate connection without shorting. The paper spacers 54 do not extend into the cutout. Therefore, the cathodes, like the anodes, may be connected together in parallel when the tabs are brought together in a bundle.

Figure 4:
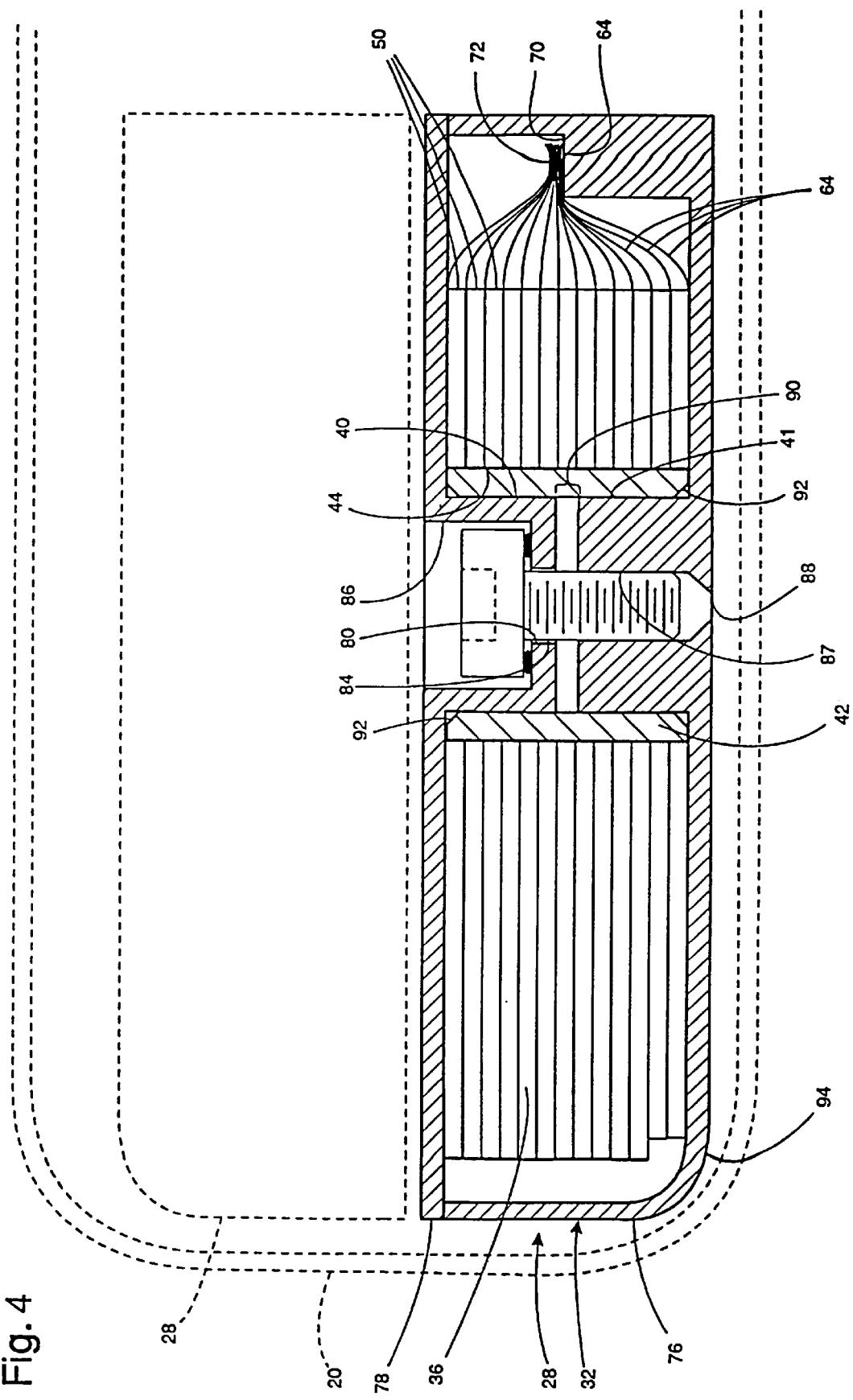
FIG. 4 is a cross sectional side view taken along line 4—4 of FIG. 2.

The anode tabs 60 are compressed together and welded together at their free ends, such as with a YAG laser. The welded anode tab bundle is then welded to an inner terminal 66 of an anode post 68 that passes through a wall of the capacitor housing. The anode post 68 is electrically insulated from the housing. The cathode tabs 64 are electrically connected to the capacitor housing. A cathode lead 69 provides an external electrical connection to the housing. The cathode tabs 64 are ultrasonically welded to a housing step 70 abutting the periphery of the interior of the housing. As shown in FIG. 4, the step height is about half the height of the stack 36, so that the top and bottom cathode sheets need not be excessively deflected. An ultrasonic tool compresses the cathode tabs against the step at a weld point 72, and imparts ultrasonic energy to provide a secure electrical and mechanical connection.

As shown in FIG. 4, the housing 32 of the capacitor 28 includes a pan-shaped base 76, and a flat lid 78 overlaying the base and resting on the base's upper rim. The alignment boss 40 on the lid includes a through-hole 80 for receiving a fastener shank 84, and a counter bore 86 to provide a recess so that the fastener head does not protrude above the surface of the housing. An O-ring or gasket may provide a seal between the fastener head and counter bore surface to prevent leakage of electrolyte from the capacitor. The boss 41 on the base 76 defines a threaded hole 87 for receiving the fastener screw, and has an alignment aperture 88 which is a blind tapped hole at the lower surface of the housing. The aperture 88 also provides a registration hole or alignment index for precise engagement by manufacturing fixtures. This permits position sensitive processes such as welding to be achieved by a simple automated system not requiring pattern recognition vision systems for alignment. Although the fastener is shown as a machine screw in a threaded bore, rivets or other mechanical fasteners may be used.

The insulating sleeve 42 closely encompasses both bosses 40, 41 to ensure concentric alignment of the bosses. The sleeve has a sufficient length or height to extend from the floor of the base to the ceiling of the lid, contacting both. Thus, while the periphery of the housing lid rests upon the rim of the housing base, the center of the lid rests upon the sleeve ends. The absence of a gap between the sleeve ends and the base or lid of the housing prevents one layer of the capacitor stack from shifting and potentially shorting the anode to the boss. The bosses 40, 41 are short enough to define a gap 90 between their opposed ends, ensuring that the sleeve is compressed between the lid and base by the force of the fastener. Even a slight deflection of the lid to a dished shape is tolerated to ensure contact with the sleeve ends. This contact also serves as an additional seal to prevent leakage of electrolyte fluid at the fasteners. The sleeve includes an inner chamfer 92 at each end to avoid interference with any radius remaining at the base of either boss. Although the lid is secured by fasteners, the housing must be sealed to prevent leakage of electrolyte solution that fills the housing. This is achieved by laser welding the entire periphery after assembly. The alignment apertures 88 provide effective alignment for this operation.

In the preferred embodiment, two capacitors are installed in a single defibrillator unit. The capacitors are stacked with their lids face-to-face. Because the defibrillator housing 20 has radiused edges for a physiologic shape appropriate to an implanted device, the capacitor housing has a 0.070 inch radiused edge 94 about a portion of its lower periphery. This permits a pair of capacitors to efficiently fill the defibrillator housing 20. So that the capacitor layers efficiently fill the capacitor housing, the lowest two layers have reduced peripheries to avoid abutting the radius. The remaining layers extend closer to the housing wall to maximize capacitance for a given housing volume, with the preferred spacing being about 0.034 inch.

In the preferred embodiment, the overall thickness of one capacitor is 0.212 inch, the average capacitance area is 41.8 square inches, providing an overall capacitor volume of 0.38 cubic inches. The two capacitors, each having a value of approximately 290 $\mu$F, provide a total source capacitance in the device of 145 $\mu$F. Consequently, a stored energy density of about 3.3 J/cm$^3$ is provided. While the invention is described in terms of a preferred embodiment, the following claims are not intended to be so limited.

What is claimed is:

1. A method for making a layered capacitor comprising the steps of:

providing a conductive housing defining a chamber and including a housing step at a peripheral portion of said chamber;

positioning a plurality of planar charge storing layers within said chamber, each layer including at least a cathode sheet, a separator and an anode foil, each of said cathode sheets including a cathode tab extending from said cathode sheet; and ultrasonically welding said cathode tabs to said housing step.

2. The method of claim 1 wherein said step of ultrasonically welding includes the step of compressing said cathode tabs against said housing step at a weld point and imparting ultrasonic energy.

* * * * *